(12) United States Patent
Helton et al.

(10) Patent No.: US 8,637,263 B1
(45) Date of Patent: Jan. 28, 2014

(54) ASSAY FOR DETERMINATION OF COMPOUNDS HAVING ANTI-EMETIC ACTIVITY

(75) Inventors: David Reed Helton, Dana Point, CA (US); David Brian Fick, Coto de Caza, CA (US); Ernest H. Pfadenhauer, Costa Mesa, CA (US)

(73) Assignee: Epiomed Therapeutics, Inc., Laguna Hills, CA (US)

( * ) Notice: Subject to any disclaimer, the term of this patent is extended or adjusted under 35 U.S.C. 154(b) by 153 days.

(21) Appl. No.: 13/274,106

(22) Filed: Oct. 14, 2011

Related U.S. Application Data (60) Provisional application No. 61/393,345, filed on Oct. 14, 2010.

(51) Int. Cl.
*G01N 33/53* (2006.01)
(52) U.S. Cl.
USPC .......................................................... 435/7.2

(58) Field of Classification Search
None
See application file for complete search history.

(56) References Cited

U.S. PATENT DOCUMENTS

2012/0196301 A1* 8/2012 Garcia-Ladona et al. ... 435/7.21

OTHER PUBLICATIONS

Horn, Charles, "Is there a need to identify new anti-emetic drugs?" Drug Discov Today Ther Strateg., 2007, 4(3):183-187.

\* cited by examiner

*Primary Examiner* — Michael Pak
(74) *Attorney, Agent, or Firm* — Michael Fedrick; Loza & Loza, LLP

(57) ABSTRACT

A screening method for identifying compounds with anti-emetic properties by evaluating binding affinity and efficacy of the compounds with respect to the $5\text{-HT}_{1a}$, $5\text{-HT}_{1d}$, and $5\text{-HT}_7$ receptors.

15 Claims, 4 Drawing Sheets

ASSAY FOR DETERMINATION OF COMPOUNDS HAVING ANTI-EMETIC ACTIVITY

CROSS-REFERENCE TO RELATED APPLICATIONS

This patent application claims the benefit of priority from U.S. Patent Application No. 61/393,345, filed on Oct. 14, 2010 and entitled ASSAY FOR DETERMINATION OF COMPOUNDS HAVING ANTI-EMETIC ACTIVITY. The disclosure of this application is hereby incorporated by reference herein in its entirety.

BACKGROUND

Screening for compounds that may provide a therapeutic benefit can involve assays based upon the relationship between cell surface receptors and their natural binding partners, or ligands. In general, such assays are often developed which measure some biological signal caused by the binding of the ligand to the receptor. Compounds are then screened to determine those that can bind to the receptor, by blocking the binding of the ligand thereto, and determining what type of signal is caused by the compound—for example, the signal can be enhanced (sometimes referred to as an "agonist") or the signal can be decreased (sometimes referred to as an "antagonist). Compounds evidencing the desired binding and biological signal are then often tested in animals to determine if these compounds may provide a therapeutic benefit to humans (and in some cases, animals for animal therapeutics).

One condition for which only a limited number of medicinal remedies are currently available is emesis. Emesis (vomiting) is a common symptom of a variety of disorders, brought on by events including the administration of chemotherapeutic agents, motion, pregnancy (morning sickness), and infections. As unpleasant as emesis and the related sensation of nausea may be, they are important in many cases for survival. Emesis is often triggered by the introduction of poisons into the body, such that the body must rapidly eject such poison from the body. Not all species are capable of an emetic response. For example, rats are incapable of having emesis induced by agents that they ingest, which is the main reason why rats that eat poison cannot remove the poison from their bodies, and thus die. In humans, anti-emetic therapy generally involves removing the offending stimulus or resolving the condition responsible for the emesis.

Current therapeutic agents for emesis often have undesired side effects, such as sedation or anxiety. As such, there is a need for improved anti-emetic compounds are necessary (see, e.g., Horn, Charles, C. "Is there a need to identify new anti-emetic drugs?" *Drug Discov Today Ther Strateg.* 2007; 4(3): 183-187).

SUMMARY

The present invention addresses the need for improved treatments for emesis, in particular treatments with improved side effect profiles, providing novel and improved screening techniques to secure compounds that produce these benefits. The present screening method identifies compounds that, based upon their receptor-binding profiles, evidence anti-emetic properties while at the same time avoiding or reducing the associated side effect(s) of anxiety. Our invention is based upon the discovery of the importance role of the $5\text{-}HT_{1d}$ receptor in the screening process, as well as the importance of the role of the $5\text{-}HT_7$ receptor in this process. We have discovered that compounds which function as agonists to the $5\text{-}HT_{1a}$ and $5\text{-}HT_{1d}$ receptors lead to the understanding of compounds having anti-emetic properties, while also having little or no anxiety side effects. In this context, those compounds that also act as antagonist to the $5\text{-}HT_7$ receptor are also preferred.

The present method for identifying compounds having anti-emetic properties comprises:

(a) contacting a non-endogenous candidate compound with a serotonin receptor selected from the group consisting of:
  (i) an endogenous version of a $5\text{-}HT_{1a}$ receptor;
  (ii) a non-endogenous version of a $5\text{-}HT_{1a}$ receptor;
  (iii) an endogenous version of a $5\text{-}HT_{1d}$ receptors; and
  (iv) a non-endogenous version of a $5\text{-}HT_{1d}$ receptor;

(b) determining the binding affinity of the candidate compound for the serotonin receptor of step (a);

(c) contacting the candidate compound selected from step (b) with a serotonin receptor selected from the group consisting of:
  (i) an endogenous version of a $5\text{-}HT_{1a}$ receptor;
  (ii) a non-endogenous version of a $5\text{-}HT_{1a}$ receptor;
  (iii) an endogenous version of a $5\text{-}HT_{1d}$ receptor; and
  (iv) a non-endogenous version of a $5\text{-}HT_{1d}$ receptor,
  with the proviso that
   (A) when serotonin receptor of step (a) is selected from the group consisting of (i) an endogenous version of a $5\text{-}HT_{1a}$ receptor or (ii) a non-endogenous version of a $5\text{-}HT_{1a}$ receptor, the serotonin receptor of step (c) is selected from the group consisting of (i) an endogenous version of a $5\text{-}HT_{1d}$ receptor; and (ii) a non-endogenous version of a $5\text{-}HT_{1d}$ receptor, or
   (B) when serotonin receptor of step (a) is selected from the group consisting of (i) an endogenous version of a $5\text{-}HT_{1d}$ receptor or (ii) a non-endogenous version of a $5\text{-}HT_{1d}$ receptor, the serotonin receptor of step (c) is selected from the group consisting of (i) an endogenous version of a $5\text{-}HT_{1a}$ receptor; and (ii) a non-endogenous version of a $5\text{-}HT_{1a}$ receptor;

(d) determining the binding affinity of the candidate compound for the serotonin receptor of step (c);

(e) determining the compound efficacy of the compound of step (d) for a serotonin receptor selected from the group consisting of:
  (i) an endogenous version of a $5\text{-}HT_{1a}$ receptor;
  (ii) a non-endogenous version of a $5\text{-}HT_{1a}$ receptor;
  (iii) an endogenous version of a $5\text{-}HT_{1d}$ receptor; and
  (iv) a non-endogenous version of a $5\text{-}HT_{1d}$ receptor;

(f) determining the compound efficacy of the compound of step (e) for a serotonin receptor selected from the group consisting of:
  (i) an endogenous version of a $5\text{-}HT_{1a}$ receptor;
  (ii) a non-endogenous version of a $5\text{-}HT_{1a}$ receptor;
  (iii) an endogenous version of a $5\text{-}HT_{1d}$ receptor; and
  (iv) a non-endogenous version of a $5\text{-}HT_{1d}$ receptor,
  with the proviso that:
   (A) when serotonin receptor of step (e) is selected from the group consisting of (i) an endogenous version of a $5\text{-}HT_{1a}$ receptor or (ii) a non-endogenous version of a $5\text{-}HT_{1a}$ receptor, the serotonin receptor of step (f) is selected from the group consisting of (i) an endogenous version of a $5\text{-}HT_{1d}$ receptor; and (ii) a non-endogenous version of a $5\text{-}HT_{1d}$ receptor, or (B) when serotonin receptor of step (e) is selected from the group consisting of (i) an endogenous version of a 5-HT$_{1d}$ receptor or (ii) a non-endogenous version of a 5-HT$_{1d}$ receptor, the serotonin receptor of step (f) is selected from the group consisting of (i) an endogenous version of a 5-HT$_{1a}$ receptor; and (ii) a non-endogenous version of a 5-HT$_{1a}$ receptor.

Preferably, based upon step (e) and step (f), the candidate compound is an agonist. In particularly preferred embodiments of our invention, the compound of step (f) is:

(g) further contacted with a serotonin receptor selected from the group consisting of:
(i) an endogenous version of a 5-HT$_7$ receptor; and
(ii) a non-endogenous version of a 5-HT$_7$ receptor,
followed by determining if the compound has activity selected from the group consisting of (i) no binding activity at said receptor and (ii) binding activity at said receptor; and when the compound has binding activity at said receptor, determining the compound efficacy of the compound of step (g) by contacting the compound with a serotonin receptor selected from the group consisting of:
(i) an endogenous version of a 5-HT$_7$ receptor; and
(ii) a non-endogenous version of a 5-HT$_7$ receptor Ideally, a candidate compound has no binding activity at the 5-HT$_7$ receptor. In cases where there is binding affinity at this receptor, it is preferred that the candidate compound be further screened for determination of compound efficacy, and such compound is preferable determined to be an antagonist.

In some embodiments of the invention, the non-endogenous versions of the receptors are constitutively activated. In other embodiments of the invention, compounds known to be agonists to the 5-HT$_{1a}$ receptor are screened to determine both the agonist binding affinity for the 5-HT$_{1d}$ receptor and the compound efficacy of the agonist compound for the 5-HT$_{1d}$ receptor. These compounds can then be further screened to determine both the antagonist binding affinity for the 5-HT$_7$ receptor and, when necessary, the compound efficacy of the antagonist compound for the 5-HT$_7$ receptor.

In one preferred embodiment, the present invention comprises a method for screening candidate compounds, comprising the steps of:

contacting one or more candidate compounds with a 5-HT$_{1a}$ receptor and determining the binding affinity and compound efficacy of the candidate compounds with respect to binding of the 5-HT$_{1a}$ receptor;

contacting one or more candidate compounds with a 5-HT$_{1d}$ receptor and determining the binding affinity and compound efficacy of the candidate compounds with respect to binding of the 5-HT$_{1d}$ receptor;

contacting one or more candidate compounds with a 5-HT$_7$ receptor and determining the binding affinity and compound efficacy of the candidate compounds for the 5-HT$_7$ receptor; and selecting a candidate compound, wherein the selected candidate compound is an agonist of at least one of the 5-HT$_{1a}$ receptor and the 5-HT$_{1d}$ receptor, and wherein the selected candidate compound is an antagonist of the 5-HT$_7$ receptor or has an EC$_{50}$ value for the 5-HT$_7$ receptor of greater than about 10 µM.

Preferably the selected candidate compound does not bind to the 5-HT$_7$ receptor. Selected candidate compounds are also preferably formulated as pharmaceutical compositions, manufactured, and then administered to subjects in need thereof.

DESCRIPTION

As used herein, the following terms and variations thereof have the meanings given below, unless a different meaning is clearly intended by the context in which such term is used.

"8-(OH)-DPAT" refers to (±)-8-Hydroxy-2-(dipropylamino)tetralin.

"About" when used in reference to a numerical value means plus or minus ten percent of the indicated amount. For example and not by way of limitation, "about 10" means between 9 and 11, and "about 10%" means between 9% and 11%.

"Agonist" means molecule or material (e.g., ligands, candidate compounds) that activates the intracellular response when it binds to a receptor.

"Partial agonist" means molecule or material (e.g., ligands, candidate compounds) that activates an intracellular response when it binds to a receptor to a lesser degree/extent than do agonists, or enhances GTP binding to membranes to a lesser degree/extent than do agonists.

"Antagonist" means a molecule or material (e.g., ligands, candidate compounds) that competitively binds to a receptor at the same site as an agonist but which does not activate the intracellular response initiated by the active form of the receptor, and can thereby inhibit the intracellular responses by agonists or partial agonists. Antagonists do not diminish the baseline intracellular response in the absence of an agonist or partial agonist.

"Anticipatory emesis" means a conditioned vomiting response, i.e. emesis that occurs in a subject before the subject is exposed to a substance, agent, or event (such as exposure to a chemotherapeutic agent) which has previously caused the subject to experience emesis.

"Anxiety" means a sense of apprehension and fear often marked by physical symptoms (such as sweating, tension, and increased heart rate). Anxiety can be measured in clinical and preclinical models known to those having scientific skill, knowledge and experience in these areas.

"Anxiogenic" means a substance, agent, event, or condition that causes anxiety.

"Binding Affinity" means the affinity of a compound to bind with a receptor due to intermolecular forces between the compound and the receptor, which affect the residence time for the compound at the receptor binding site.

"Candidate Compound" means a molecule, compound, or other material being screened according to the present methods. Candidate compounds can be, for example, a small molecule (e.g., a chemical compound) or a biological compound (e.g., a peptide), preferably a non-naturally occurring biological compound.

"Composition" means a material comprising at least one component. A "pharmaceutical composition" is an example of a composition.

"Compound efficacy" means a measurement of the ability of a compound to inhibit or stimulate an effect or functionality mediated by a receptor. Compound efficacy can be used to determine if a candidate compound is, for example, an agonist, antagonist, or inverse agonist.

"Constitutively activated receptor" means a receptor receptor which is capable of producing its biological response in the absence of a bound ligand. A constitutively activated receptor can be endogenous or non-endogenous.

"Constitutive receptor activation" means stabilization of a receptor in the active state by means other than binding of the receptor with its endogenous ligand or a chemical equivalent thereof.

"Contact" or "Contacting" means placing a moiety, molecule, compound, or other material (a "material") in the same container, organism, solution, or other physical space or media as another material such that the materials interact or come into physical contact, or such that the materials at least have an opportunity to interact or make physical contact. In the present methods such contact can be in an in vitro system or an in vivo system.

"Delayed emesis" means emesis that occurs in a subject more than 24 hours after the subject is exposed to a substance, agent, or event which results in the subject experiencing emesis, or that occurs more than 24 hours after the subject contracts a condition which results in the subject experiencing emesis.

"Emesis" means vomiting, i.e., the reflex act of ejecting the contents of the stomach through the mouth.

"Enantiomer" means a compound that is one of two stereoisomers that are nonsuperimposable complete mirror images of each other.

"Enantiomeric excess" means a composition in which one enantiomer is present in an amount which exceeds the amount of the other entantiomer in the composition, and is defined as the absolute difference between the mole fraction of each enantiomer. This can be expressed formulaically as follows:

$$ee = |F_+ - F_-|$$

where $$F_+ + F_- = 1.$$

"Endogenous" means a material that a subject, in particular a mammal, naturally produces. Endogenous in reference to, for example and not limitation, the term "receptor," means that which is naturally produced by a subject (for example, and not limitation, a human) or is found in the subject, for example by being introduced by a virus. By contrast, the term "Non-Endogenous" in this context means that which is not naturally produced by or found in a subject (for example, and not limitation, a human). For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, in a screening approach, the endogenous or non-endogenous receptor can be in reference to an in vitro screening system. As a further example and not limitation, where the genome of a mammal has been manipulated to include a non-endogenous constitutively activated receptor, screening of a candidate compound by means of an in vivo system is viable.

"Inverse Agonist" means materials (e.g., ligands, candidate compounds) which bind to either the endogenous form of a receptor or to the constitutively activated form of the receptor, and which inhibit the baseline intracellular response initiated by the active form of the receptor below the normal base level of activity which is observed in the absence of agonists or partial agonists, or which decrease GTP binding to membranes. Preferably, the baseline intracellular response is inhibited in the presence of an inverse agonist by at least 30%, more preferably by at least 50%, and most preferably by at least 75%, as compared with the baseline response in the absence of the inverse agonist.

"Ligand" means an endogenous, naturally occurring molecule specific for an endogenous, naturally occurring receptor.

"Nausea" means a sensation of unease and discomfort in the stomach accompanied by an urge to vomit. Nausea can be measured in ways known to the art, such as through the use of a visual analog scale (VAS).

"No Binding Activity" means that the Ki of a candidate compound for a receptor is greater than about 10 micromolar. In this context, the "Ki" means a constant whose numerical value depends on the equilibrium between the un-dissociated and dissociated forms of a ligand or candidate compound for a receptor, whereby a higher value indicates greater dissociation, e.g., no or almost no affinity of a candidate compound for a receptor.

"Percent enantiomeric excess" means the enantiomeric excess expressed as a percentage. For example, a sample with 70% of S isomer and 30% of R will have an enantiomeric excess of 40%. This can also be thought of as a mixture of 40% pure S with 60% of a racemic mixture (which contributes 30% R and 30% S to the overall composition).

"Pharmaceutical composition" means a composition comprising at least one active ingredient, whereby the composition is amenable to investigation for a specified, efficacious outcome in a subject (for example, and not limitation, a human). Those of ordinary skill in the art will understand and appreciate the techniques appropriate for determining whether an active ingredient has a desired efficacious outcome based upon the needs of the subject.

"Treat" and "treatment" refer to a medical intervention which attenuates, prevents, or cures a medical condition. In the context of addressing emesis by administering one of the compositions identified with the present methods, both prophylactic treatment and the treatment of emesis after a subject experiences emesis are included. Prophylactic treatment includes administration of a composition before a subject experiences emesis, such as when the subject experiences nausea, as well as administration of the composition before the subject is exposed to a substance, agent, or event, or before the subject contracts a condition, which results in or is likely to result in the subject experiencing emesis.

As used herein, the term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Methods for creating non-endogenous versions of the receptors used in the disclosed assays are known to those in the art using standard biological tools and techniques. Methods for creating constitutively activated, non-endogenous versions of the receptors used in the disclosed assays are also known to those in the art using standard biological tools and techniques. Preferred methods for creating constitutively active, non-endogenous receptors used in the disclosed assays are set forth in U.S. Pat. No. 6,555,339, for example.

Anti-Emetic Assays

In the area of anti-emetic compounds, the serotonin receptors are thought to play a significant role, although other receptors have also been utilized for the development of anti-emetic compounds (for example NK-1, NK-3, Ghrelin, etc.). There are multiple serotonin receptor subtypes, meaning, there are different receptors having different biological functional activities but which all bind with the endogenous neurotransmitter serotonin (5-hydroxytryptamine, 5-HT). With the exception of 5-HT3 receptors, all other serotonin receptors are part of a class of receptors referred to as G protein-coupled receptors (GPCRs).

Because the serotonin receptors have in common, for example, the same ligand, i.e., serotonin, challenges exist for screening of compounds to interact with a desired receptor sub-type. There are currently 7 known serotonin receptors, referred to as $5-HT_{1-7}$, and of these, multiple sub-types exist. For example, for the $5-HT_1$ receptor, there are 5 different sub-types that are known, and each of these is associated with diverse and unrelated biological activities, as is well known and understood by researchers in this field. The $5-HT_{1a}$ receptor is one such subtype of serotonin receptors and has been utilized as a target for screening of compounds having anti-emetic activity, i.e. U.S. Pat. No. 4,943,428. Critically, a compound that binds with one serotonin subtype to provide a positive therapeutic benefit may also bind with other serotonin receptor sub-types to produce undesirable side effects. For example, flexinoxan is a full $5-HT_{1a}$ receptor agonist that has evidenced the prevention of multiple-stimulus-induced emesis; however, the compound also produces the undesirable side-effect of anxiety. Marin, Jr. et al. "Long-term antidepressant treatments result in a tonic activation of forebrain $5-HT_{1a}$ receptors." *J Neurosci* 1998 Dec. 1; 18(23):10150-6.

We disclose a screening method for determining compounds that, based upon their receptor-binding profiles, evidence anti-emetic properties while at the same time avoiding or reducing the associated side effect(s) of anxiety. Our invention is based upon the discovery of the importance of the role of the $5-HT_{1d}$ receptor in the screening process, as well as the importance of the role of the $5-HT_7$ receptor in this process. We have discovered that compounds which function as agonists to the $5-HT_{1a}$ and $5-HT_{1d}$ receptors lead to the understanding of compounds having anti-emetic properties, while also having little or no anxiety side effects. In this context, those compounds that also act as antagonist to the $5-HT_7$ receptor are preferred.

Assay techniques for screening of candidate compounds are well known to those having scientific skill, knowledge and experience in this field. While these assays can be readily developed based on scientific literature and commercially available materials, reagents and testing equipment, such assays are generally commercially available for purchase and use. Our invention is not based upon specific assay techniques or procedures, but rather what particular receptors are to be used for assay screening, and the characteristics for the candidate compounds derived from the screening assays. In this context, screening assays for screening candidate compounds can be developed when needed using standard, well-known techniques, or purchased from scientific vendors who develop and sell assay kits to perform screening assays, or secured from outside organizations which screen candidate compounds against the receptors disclosed herein. One such organization is Cerep (Cerep USA Laboratories, 15318 N.E 95th Street, Redmond, Wash., 98052), an international organization that conducts screening services for its clients in the scientific community.

With respect to receptor-based screening assays, candidate compounds are often initially screened to determine if the compounds bind with the receptor using competitive binding assays, that is, assays designed to typically measure the ability of the candidate compound to compete with the receptor's ligand for binding to the receptor. However, binding affinity alone is often insufficient to determine the importance of a candidate compound at a receptor. As is often necessary, the compound efficacy of the compound must also be determined. Compound efficacy is often used to determine what impact the candidate compound has on the activity of the receptor to effectuate a desired biological outcome. Identifying the compound efficacy of a candidate compound is useful in identifying the type of receptor-activity, if any, that the candidate compound can have, for example, as an agonist, antagonist, or inverse agonist. Those having skill, knowledge and experience in this field are well versed in understanding these types of compound efficacies. As such, and as is well known to those having skill, knowledge and experience in these areas, while the type of binding characteristics that a candidate compound has is important, it is also important to understand the compound efficacy of the candidate compound. For example, a candidate compound may "weakly" bind to a receptor and yet be considered very potent, that is, the compound can substantially affect the biological function of the receptor despite only weakly binding to the receptor.

Once candidate compounds are screened to select for those compounds that have the required and specified characteristics, such compound(s) can be tested in animal models to assess the attributes of the compound(s) in a living animal. Those with scientific skill, knowledge and experience in this field understand the methods and procedures for the testing of candidate compounds in animal models of medical conditions, diseases or disorders. Candidate compounds that are tested in animal models can then be formulated into pharmaceutical compositions that can ultimately be evaluated in humans. Those with scientific skill, knowledge and experience in this field understand the methods and procedures for formulating pharmaceutical compositions and testing candidate compounds in subjects having conditions, diseases or disorders for which the compounds can, alone or in conjunction with other compounds and compositions, be useful in treating such conditions, diseases or disorders.

Binding affinity assays often rely upon the binding affinity of a compound, which can be expressed as the Ki of the candidate compound for that receptor. In terms of compound efficacy, a multitude of assays exist which measure different aspects of compound efficacy. For example, in the context of screening assays for GPCRs, those with scientific skill, knowledge and experience understand that assays exist for cyclic-AMP production which measure the ability of a candidate compound to impact the production of cyclic-AMP as an indication of the biological impact that the candidate compound has. However, other similar measurements can be made with different outcome measures, for example, calcium ion mobilization. In this context, those with scientific skill, knowledge and experience in this field understand that a candidate compound whose compound efficacy is measured using one type of assay can also be assayed to determine the compound efficacy of that compound using a different assay which measures, for example, a different receptor product. In this context, while we provide data based on certain assays used to determine compound efficacy with specified outcome measure, those having scientific skill, knowledge and experience in this area will understand that the invention is not limited to the specific assays and outcome measures disclosed herein.

As will be apparent to those with scientific skill, knowledge and experience in this field, it can sometimes be the case that a particular compound can have some of the characteristics of receptor binding and compound efficacy as disclosed herein, but not other characteristics. For example, a compound can be known to be a $5HT_{1a}$ agonist with the required compound efficacy characteristic, but the characteristics may be unknown with respect to the $5HT_{1d}$ and/or $5HT_7$ receptor(s). Those with scientific skill, knowledge and experience in this field, having understood the basis for our invention, will readily appreciate that screening of compounds having some of the specified characteristics disclosed herein, but not all, can be further screened for the criteria disclosed herein to arrive at compounds that fall within the scope of our invention.

With the foregoing in mind, our invention is based on the discovery of a method for identifying compounds having anti-emetic properties comprising:

(a) contacting a candidate compound, preferably a non-endogenous candidate compound, with a serotonin receptor selected from the group consisting of:
  (i) an endogenous version of a $5\text{-}HT_{1a}$ receptor;
  (ii) a non-endogenous version of a $5\text{-}HT_{1a}$ receptor;
  (iii) an endogenous version of a $5\text{-}HT_{1d}$ receptors; and
  (iv) a non-endogenous version of a $5\text{-}HT_{1d}$ receptor;
(b) determining the binding affinity of the candidate compound for the serotonin receptor of step (a);
(c) contacting the candidate compound selected from step (b) with a serotonin receptor selected from the group consisting of:
  (i) an endogenous version of a $5\text{-}HT_{1a}$ receptor;
  (ii) a non-endogenous version of a $5\text{-}HT_{1a}$ receptor;
  (iii) an endogenous version of a $5\text{-}HT_{1d}$ receptor; and
  (iv) a non-endogenous version of a $5\text{-}HT_{1d}$ receptor,
  with the proviso that
    A. when serotonin receptor of step (a) is selected from the group consisting of (i) an endogenous version of a $5\text{-}HT_{1a}$ receptor or (ii) a non-endogenous version of a $5\text{-}HT_{1a}$ receptor, the serotonin receptor of step (c) is selected from the group consisting of (i) an endogenous version of a $5\text{-}HT_{1d}$ receptor; and (ii) a non-endogenous version of a $5\text{-}HT_{1d}$ receptor, or
    B. when serotonin receptor of step (a) is selected from the group consisting of (i) an endogenous version of a $5\text{-}HT_{1d}$ receptor or (ii) a non-endogenous version of a $5\text{-}HT_{1d}$ receptor, the serotonin receptor of step (c) is selected from the group consisting of (i) an endogenous version of a $5\text{-}HT_{1a}$ receptor; and (ii) a non-endogenous version of a $5\text{-}HT_{1a}$ receptor;
(d) determining the binding affinity of the candidate compound for the serotonin receptor of step (c);
(e) determining the compound efficacy of the compound of step (d) for a serotonin receptor selected from the group consisting of:
  (i) an endogenous version of a $5\text{-}HT_{1a}$ receptor;
  (ii) a non-endogenous version of a $5\text{-}HT_{1a}$ receptor;
  (iii) an endogenous version of a $5\text{-}HT_{1d}$ receptors; and
  (iv) a non-endogenous version of a $5\text{-}HT_{1d}$ receptor;
(f) determining the compound efficacy of the compound of step (e) for a serotonin receptor selected from the group consisting of:
  (i) an endogenous version of a $5\text{-}HT_{1a}$ receptor;
  (ii) a non-endogenous version of a $5\text{-}HT_{1a}$ receptor;
  (iii) an endogenous version of a $5\text{-}HT_{1d}$ receptor; and
  (iv) a non-endogenous version of a $5\text{-}HT_{1d}$ receptor,
  with the proviso that:
    A. when serotonin receptor of step (e) is selected from the group consisting of (i) an endogenous version of a $5\text{-}HT_{1a}$ receptor or (ii) a non-endogenous version of a $5\text{-}HT_{1a}$ receptor, the serotonin receptor of step (f) is selected from the group consisting of (i) an endogenous version of a $5\text{-}HT_{1d}$ receptor; and (ii) a non-endogenous version of a $5\text{-}HT_{1d}$ receptor, or
    B. when serotonin receptor of step (e) is selected from the group consisting of (i) an endogenous version of a $5\text{-}HT_{1d}$ receptor or (ii) a non-endogenous version of a $5\text{-}HT_{1d}$ receptor, the serotonin receptor of step (f) is selected from the group consisting of (i) an endogenous version of a $5\text{-}HT_{1a}$ receptor; and (ii) a non-endogenous version of a $5\text{-}HT_{1a}$ receptor.

In particularly preferred embodiments of our invention, the compound of step (f) is:

(g) further contacted with a serotonin receptor selected from the group consisting of:
  (i) an endogenous version of a $5\text{-}HT_7$ receptor; and
  (ii) a non-endogenous version of a $5\text{-}HT_7$ receptor;

followed by determining if the candidate compound has activity selected from the group consisting of (i) no binding activity at said receptor and (ii) binding activity at said receptor; and when the compound has binding activity at this receptor, determining the compound efficacy of the compound by contacting it with a serotonin receptor selected from the group consisting of:
  (i) an endogenous version of a $5\text{-}HT_7$ receptor; and
  (ii) a non-endogenous version of a $5\text{-}HT_7$ receptor Ideally, the candidate compound has no binding activity at the $5\text{-}HT_7$ receptor. In cases where the candidate compound has binding affinity for this receptor, it is preferred that the candidate be further screened for determination of compound efficacy, and that the compound act as an antagonist to this receptor.

With respect to binding affinity, most preferably this is based on the Ki of the candidate compound, a standard measure understood and routinely utilized by those having skill, knowledge and experience in this field. With respect to the receptors of our invention, our Ki preferences are set forth in Table I as follows:

TABLE I

| Receptor | Preference | Ki Range (nanomolar) |
| --- | --- | --- |
| $5\text{-}HT_{1a}$ | Preferred | 0.01-100 |
|  | More Preferred | 0.05-10.0 |
|  | Most Preferred | 0.20-1.00 |
| $5\text{-}HT_{1d}$ | Preferred | 0.10-10,000 |
|  | More Preferred | 0.50-1000 |
|  | Most Preferred | 1.00-100 |

With respect to the $5\text{-}HT_7$ receptor, the candidate compound preferably has no binding affinity for the receptor. In cases where the binding constant is less than 10 micromolar, our preference is that a candidate compound that falls within the range of our disclosed binding affinity preferences for both the $5\text{-}HT_{1a}$ and $5\text{-}HT_{1d}$ be assayed for the compound efficacy thereof with respect to the $5\text{-}HT_7$ receptor, as we disclose below.

Binding assays for $5\text{-}HT_{1a}$, $5\text{-}HT_{1d}$, and $5\text{-}HT_7$ are commercially available and can be obtained, for example, from Cerep USA Laboratories. A 5-$HT_{1a}$ assay is also described in Mulhereon et al. (1994) *J. Biol. Chem.*, 269: 12954-12962, while a 5-$HT_{1d}$ assay is described in Wurch et al. (1997) *J. Neurochem.*, 68: 410-418. A 5-$HT_7$ binding assay can be found in Shen et al. (1993) *J. Biol. Chem.*, 268: 18200-18204.

In terms of compound efficacy, our characteristic preference for the receptors is, when applicable, as set forth in Table II as follows:

TABLE II

| Receptor | Compound Efficacy Characteristic |
|---|---|
| 5-$HT_{1a}$ | Agonist |
| 5-$HT_{1d}$ | Agonist |
| 5-$HT_7$ (when applicable) | Antagonist |

In terms of determining the compound efficacy, those with scientific skill, knowledge and experience in this area often measure the compound efficacy in terms of $EC_{50}$, that is, the molar concentration of the candidate compound which produces 50% of the maximum possible effective response for that compound. While $EC_{50}$ is the measurement used to determine compound efficacy, there are many ways to determine this value. Thus, one assay type may produce one $EC_{50}$ value and another assay type may produce another $EC_{50}$ value for that assay. These can be based on products produced by the receptor when contacted with a candidate compound. The produced product generates a signal, and this signal is measured, and most often compared to the signal measured based upon binding of the ligand to the receptor. An example of one such product measured in GPCR assays is cyclic-AMP, as is well known to those with skill, knowledge and experience in this field. The candidate compound can therefore be assayed using different assays to determine an $EC_{50}$ value such that those having skill, knowledge and experience in this field understand that to secure comparative results, the same assay, most preferably based upon the same assay protocol, must be used to determine a comparative $EC_{50}$ value.

With respect to compound efficacy, $EC_{50}$ preferences are set forth in Table III as follows:

TABLE III

| Receptor | Assay Type (Preferred Source) | Preference | $EC_{50}$ Range (nanomolar) |
|---|---|---|---|
| 5-$HT_{1a}$ | Ca2+ Mobilization (1) | Preferred | 0.01-100 |
| | | More Preferred | 0.05-10.0 |
| | | Most Preferred | 0.20-1.00 |
| 5-$HT_{1d}$ | Impedance (2) | Preferred | 0.10-10,000 |
| | | More Preferred | 0.50-1,000 |
| | | Most Preferred | 1.00-100 |

Assays for determining the $EC_{50}$ values for the receptors can be determined with commercially available assays from Cerep USA Laboratories, for example, and can be performed according to Newman-Tancredi et al. (2001) *Brit. J. Pharmacol.*, 132: 518-524 or Wurch et al. (1997) *J. Neurochem.*, 68: 410-418.

With respect to the 5-$HT_7$ receptor, in such cases where the candidate compound evidences all of the criteria set for the herein with respect to the 5-$HT_{1a}$ and 5-$HT_{1d}$ receptors, the binding affinity for the 5-$HT_7$ receptor but the candidate compound is determined to have agonist activity at the 5-$HT_7$ receptor, we prefer that the candidate compound evidence an $EC_{50}$ value for the 5-$HT_7$ of greater than about 10 µM, using cyclic-AMP as the measured product. With respect to the assay type for the 5-$HT_7$ receptor, a preferred assay can be secured from Cerep USA Laboratories, with further reference to Adham et al. (1998) *J. Pharmacol. Exp. Ther.*, 287: 508-514.

Candidate compounds screened using the foregoing assays at the specified receptors and securing measured outcome-values as disclosed herein can be developed as compositions and further tested in animals to confirm that such compounds can function therapeutic compounds, such as anti-emetic compounds, that have reduced or no anxiety side effects. Such compounds can then be further evaluated in humans. In addition to treating emesis, such compounds can be screened for other therapeutic effects, in particular those associated with binding or activity of the 5-$HT_{1a}$ receptor or the 5-$HT_{1d}$ receptor. Once an appropriate candidate is identified, it can be manufactured by methods known to those of skill in the art.

One or more of the candidate compounds that meet the criteria disclosed herein, once manufactured or otherwise produced, can then be provided as composition(s) to a mammal such as a human in need thereof. In the treatment of emesis, such composition(s) can be beneficial in the treatment of acute, delayed or anticipatory emesis, including emesis induced by chemotherapy, radiation, toxins, viral or bacterial infections, pregnancy, vestibular disorders (e.g. motion sickness, vertigo, dizziness and Meniere's disease), surgery, migraine, and variations in intracranial pressure. The use of such compositions is also of benefit in the therapy of emesis induced by radiation, for example during the treatment of cancer, and in the treatment of post-operative nausea and vomiting. The use of such compositions is also beneficial in the therapy of emesis induced by antineoplastic (cytotoxic) agents including those routinely used in cancer chemotherapy, and emesis induced by other pharmacological agents. Further, the use of such compositions can also be used in the therapy of acute, delayed or anticipatory emesis from an unknown cause. In addition to treating emesis, such compositions can be used to treat nausea.

Screening Results

Based on the foregoing, we identified an anti-emetic composition by screening 8-OH-DPAT enantiomers using the assays set forth above. 8-OH-DPAT enantiomers were obtained from ChemPacific (Baltimore, Md. USA) and provided by us to Cerep for purposes of the screening. Based on these screens, the following results were obtained, as set forth in Table IV as follows:

TABLE IV

| | 8-OH-DPAT Enantiomer | | | |
|---|---|---|---|---|
| | R(+) | | S(−) | |
| Receptor | Ki (nanomolar) | Agonist $EC_{50}$ (nanomolar) | Ki (nanomolar) | Agonist $EC_{50}$ (nanomolar) |
| 5-$HT_{1a}$ | 0.62 | 0.80 | 0.50 | 0.40 |
| 5-$HT_{1d}$ | 67.00 | 14.00 | 860.00 | 420.00 |
| 5-$HT_7$ | 5.10 | 1,200.00 | 29.00 | 26,000.00 |

Based on these results, the enantiomers were determined to meet the criteria set forth above. Further evaluation in animal models was then conducted.

8-OH-DPAT Evaluation

We have found that the R-enantiomer of 8-OH-DPAT, administered alone, is 100% effective in preventing chemically-induced emesis, but has a moderate to strong anxiety-inducing effect when administered to test subjects. We have further discovered that the S-enantiomer of 8-OH-DPAT, although not fully effective in preventing chemically induced emesis when administered as a sole agent, induces no anxiety or only slight anxiety in test subjects. By altering the ratios of the R- and S-enantiomers in a mixture of 8-OH-DPAT enantiomers, therefore, the present inventors have produced a composition with improved properties. A specific combination of the S(−) and R(+) isomers of 8-OH-DPAT can be used in the treatment of emesis in a mammal, preferably a human, without anxiogenic effects.

Figure 1:
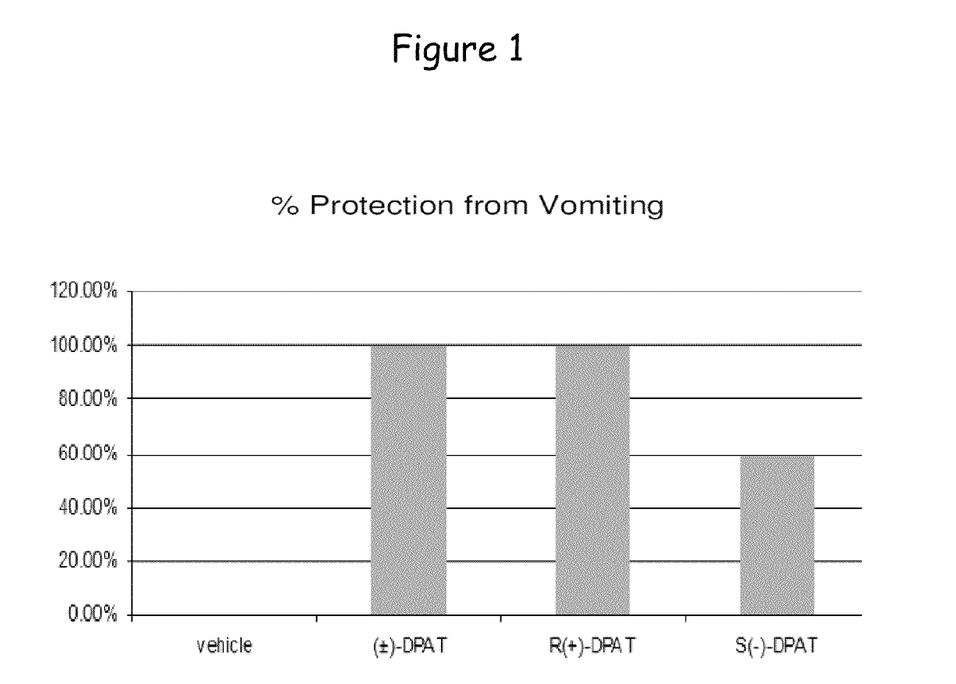
FIG. 1 is a bar graph showing the amount of protection from vomiting provided by 8-OH-DPAT compositions in female cats in a model of emesis induced by xylazine.

This conclusion is illustrated in FIG. 1, which shows data gathered from a test of female domestic short-haired felines which were subcutaneously (SC) administered either:
  (i) 0.9% sodium chloride vehicle (n=6);
  (ii) 0.16 mg/kg of (±)-8-Hydroxy-2-(dipropylamino)tetralin hydrobromide (n=6);
  (iii) 0.08 mg/kg R(+)-8-Hydroxy-2-(dipropylamino)tetralin hydrobromide (n=6); or
  (iv) 0.08 mg/kg S(−)-8-Hydroxy-2-(dipropylamino)tetralin hydrobromide (n=5).

Fifteen minutes later, 0.66 mg/kg xylazine was administered subcutaneously, and the test subjects where then observed for 30 minutes. As shown in the first bar of FIG. 1, when the 0.9% sodium chloride vehicle was administered to the cats, all the cats vomited, exhibiting 0% protection against xylazine-induced emesis, and none of the cats showed any anxiety 15 minutes after treatment with the vehicle. When the racemic mixture of (±)-8-Hydroxy-2-(dipropylamino)tetralin hydrobromide was administered to the cats, none of the cats vomited, exhibiting 100% protection against xylazine-induced emesis, but the cats showed a moderate level of anxiety 15 minutes after treatment (second bar of FIG. 1). As shown in the third bar of FIG. 1, when R(+)-8-Hydroxy-2-(dipropylamino)tetralin hydrobromide was administered to the cats as a sole agent, none of the cats vomited, but the cats showed an extreme level of anxiety 15 minutes after treatment. By contrast, when S(−)-8-Hydroxy-2-(dipropylamino)tetralin hydrobromide was administered to the cats, 40% of cats vomited, exhibiting 60% protection against xylazine-induced emesis, and the cats did not show any anxiety 15 minutes after treatment (fourth bar of FIG. 1). Accordingly, a specific combination of the S(−) and R(+) isomers of a 2-aminotetralin compound has been found to be useful for the treatment of emesis in a mammal without an anxiogenic effect.

Further testing revealed that an excess of the S-enantiomer of 8-OH-DPAT can produce a composition which blocks emesis without producing anxiety. The ratio of S- to R-enantiomers used in the present 8-OH-DPAT compositions is preferably at least greater than 2:1, and more preferably at least 4:1. A particularly preferred ratio of S- to R-8-(OH)-DPAT is an eight to one (8:1) excess of S(−) 8-OH-DPAT, which has been found to provide complete protection against emesis and no anxiety in test subjects. When administered to test subjects, the amount of S(−)-8-(OH)-DPAT administered is preferably at least 0.08 mg/kg, and more preferably between 0.08 mg/kg and 0.16 mg/kg. The amount of R(+)-8-(OH)-DPAT administered in such compositions is also preferably less than 0.04 mg/kg.

The invention can be appreciated in certain aspects with reference to the following examples, offered by way of illustration, not by way of limitation. Materials, reagents and the like to which reference is made in the following examples are obtainable from commercial sources, unless otherwise noted.

EXAMPLES

Example 1

Blocking Xylazine-Induced Emesis

I. Animal Preparation

4. Vehicle or test compound evaluation in motion sickness induced emesis: After the 15 minute subcutaneous pretreatment with either vehicle or test compound animals rode in clear plastic boxes suspended from two 0.445 m arms that rotated about the central horizontal axis at 0.28 Hz (17 rpm). Observation took place during the motion tests that last for 30 minutes of rotation followed by an additional one minute of observation at rest. Behavioral scoring was completed using the vomit scale.

II. Xylazine-Induced Emesis

Cats not susceptible to motion sickness were assigned to the xylazine testing group. Xylazine stimulates receptors on a pathway different from that used by motion sickness and thus served as a test of the generality of anti-emetic effects observed with motion testing.

Prior to the evaluation of anti-emetic compounds, the production of an emetic response by xylazine in felines was confirmed in the laboratory. Cats were injected subcutaneously with either a freshly prepared solution of 0.66 mg/kg of xylazine in 0.9% sodium chloride or 0.9% sodium chloride vehicle, both adjusted to an injection volume of 0.1 ml/kg.

One week following the confirmation of an emetic response by the cats, subject cats were given either vehicle or test compound/composition in 0.9% sodium chloride or vehicle (injection volume of 0.1 ml/kg) subcutaneously, 20 minutes before administration of xylazine. Cats were observed for 30 minutes following xylazine treatment or for 15 minutes after the last emetic episode, whichever occurred later. Animals were scored using the vomit scale developed by Suri et al., 1979. Additional experiments were separated by at least a 1 week washout period.

III. Data Collection
  A. Vomit Scale Scoring:
    1. Sal I (licking—parasympathetic): 1 pt
    2. Sal II (drool, thin/frothy—early sympathetic): 2 pts
    3. Sal III (stringy saliva, dangles—sympathetic): 4 pts
    4. Defection: 8 pts
    5. Urination: 8 pts
    6. Wretch/vomiting: 16 pts
  B. Defensive Behavior Scale:
    1. No defensiveness: normal behavior;
    2. Slight defensiveness: retreating to the rear of the cage when approached and/or growling when being carried;
    3. Moderate defensiveness: exhibiting flattened ears and trying to claw and bite when being carried;
    4. Strong defensiveness: vigorous clawing and biting to prevent being handled.

IV. Statistical Methods

Dose response curves were analyzed by Cochran's Q-test to establish significant effects. Paired comparisons were made using McNemar's test. Tests for line parallelism, relative potency and ED50 were based on least squares regression in a program for pharmacological statistics. The data from the nonparametric rating scale was analyzed using Friedman's analysis of variance model (ANOVA).

V. Results

A. Summary of Xylazine-Induced Emesis Results in Felines.

As shown below in Table V, varying doses of R-(+)-DPAT and S-(−)-DPAT were administered to cats not susceptible to motion sickness.

TABLE V

| Compound/Composition | Compound Dose (mg/kg) | Mean Latency* | % Protection (vomiting) | Mean Defensive Score | Defensive Behavior Scale | n = |
|---|---|---|---|---|---|---|
| R/S-(+/−)-DPAT | 0.16 | — | 100.00 | 2.0 | Moderate | 5 |
| R-(+)-DPAT | 0.02 | — | 100.00 | 2.0 | Moderate | 5 |
| R-(+)-DPAT | 0.04 | — | 100.00 | 3.0 | Strong | 3 |
| R-(+)-DPAT | 0.08 | — | 100.00 | 3.0 | Strong | 6 |
| S-(−)-DPAT | 0.08 | 1.58 | 75.00 | na** | None | 4 |
| S-(−)-DPAT | 0.16 | 0.82 | 85.71 | na** | None | 7 |
| S-(−)-DPAT | 0.32 | 1.00 | 80.00 | 1.0 | Slight | 5 |
| SALINE | 0.00 | 5.06 | 0.00 | 0.0 | None | 7 |
| R-(+)-DPAT + S-(−)-DPAT | 0.02 (R-(+)-DPAT)/ 0.08 (S-(−)-DPAT) | 0.74 | 83.33 | 1.0 | Slight | 6 |
| R-(+)-DPAT + S-(−)-DPAT | 0.04 (R-(+)-DPAT)/ 0.08 (S-(−)-DPAT) | 5.00 | 75.00 | 2.0 | Moderate | 4 |
| R-(+)-DPAT + S-(−)-DPAT | 0.02 (R-(+)-DPAT)/ 0.16 (S-(−)-DPAT) | 0.00 | 100.00 | 0.6 | None | 5 |
| R-(+)-DPAT + S-(−)-DPAT | 0.04 (R-(+)-DPAT)/ 0.16 (S-(−)-DPAT) | 2.23 | 40.00 | 0.6 | None | 5 |

*Latency is the mean latency to retch/vomit, in minutes.
*na = not applicable.

Example 2

Blocking Cisplatin-Induced Emesis

Further experiments were performed as outlined in Example 1 above, except that the emesis-inducing agent used in the tests was cisplatin in place of xylazine. The cats were injected subcutaneously with either cis-platin or a sodium chloride vehicle. As shown below in Table VI, an 8:1 ratio of S-(−)-DPAT to R-(+)-DPAT was administered to cats. The cats were observed and scored using the vomit scale and defensive score described above.

TABLE VI

| Compound | Mean Score | Mean Latency (min) | % Protection (vomiting) | Mean Emetic Events | Mean Defensive Score |
|---|---|---|---|---|---|
| 0.02 mg/kg R(+)-DPAT/ 0.16 mg/kg S(−)-DPAT | 19 | 251.80 | 40.00 | 2 | none |
| 0.9% sodium chloride | 27 | 62.20 | 0.00 | 8 | none |

Example 3

Blocking Motion-Induced and Chemically-Induced Emesis in Shrews

The ability of OH-DPAT compositions to block emesis was further tested in Asian house shrews (*Suncus murinus*) using both a motion-induced model of emesis and a chemically-induced model of emesis.

A. Motion-Induced Emesis

Animals for use in testing the present compounds in connection with motion-induced emesis were included only if they vomited on both of two consecutive tests prior being treated with the test compound or vehicle. Male shrews were found to be more susceptible to emesis and were used for motion studies. In addition, test subjects received one test with saline alone to test for conditioned vomiting. A repeated measures design was employed. All tests were separated by one week to prevent habituation.

Motion sickness was induced by placing animals in individual holders (10×15×12 cm) mounted on a linear reciprocating shaker. Test subjects had five minutes of acclimation followed by ten minutes of motion at 1 Hz and 30 mm excursion. The latency for each emesis event and the number of events was recorded for each shrew. The composition used in Example 2, comprising an 8:1 ratio of S-(−)-DPAT to R-(+)-DPAT, was administered subcutaneously 15 minutes before motion was initiated in doses of 0.009 mg/kg, 0.018 mg/kg, 0.036 mg/kg, and 0.08 mg/kg.

Each test was videotaped for scoring and then archived. The duration of the retch/vomit sequence for each test animal was roughly two seconds. Incidents of violent dorsoflexion with flexion/extension of the hindquarters were counted as indications of emesis with or without the presence of vomitus. Tests with the stimulus alone were conducted at the end of the dose-response curve to verify that habituation had not occurred.

Figure 2:
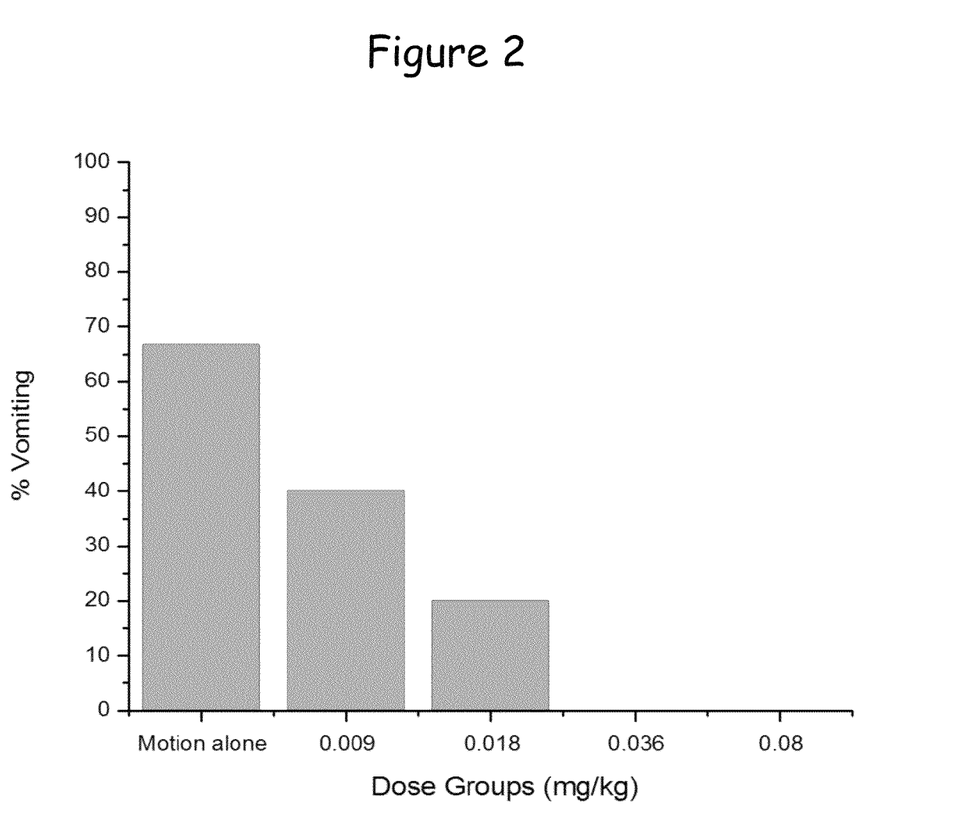
FIG. 2 is a bar graph showing the amount of protection from vomiting provided by 8-OH-DPAT compositions at varying dosages in male shrews in a model of emesis induced by motion.

The results of the foregoing tests are shown in FIG. 2. As can be seen in that figure, approximately 65% of the animals not treated with the test compound experienced emesis, while the treated animals experienced reduced or no emesis in a dose-dependent manner. Animals treated with 0.036 and 0.08 mg/kg of the test compound experienced no emesis.

B. Drug Induced Emesis

Animals evaluated in the motion-induced emesis test described above which did not evidence emesis as a result of motion, primarily female shrews, were assigned to be tested in a model of drug induced emesis. Shrews in this group received 10 mg/kg of nicotine tartarate subcutaneously and were then monitored for 30 minutes. The number of episodes of emesis and the latency for each event were recorded. The test compound used in Example 2, comprising an 8:1 ratio of S-(−)-DPAT to R-(+)-DPAT, was administered subcutaneously 15 minutes before the nicotine compound was administered. The doses of the test compound administered were 0.009 mg/kg, 0.018 mg/kg, 0.036 mg/kg, 0.058 mg/kg, and 0.08 mg/kg.

The only prodromal observation (indicating the onset of emesis) was the observation of reduced motor activity before emesis. Animals were observed for retching and emetic responses for 90 minutes post-dosing. Tests were conducted at the end of the dose-response curve involving injecting saline alone in order to look for conditioned vomiting.

Figure 3:
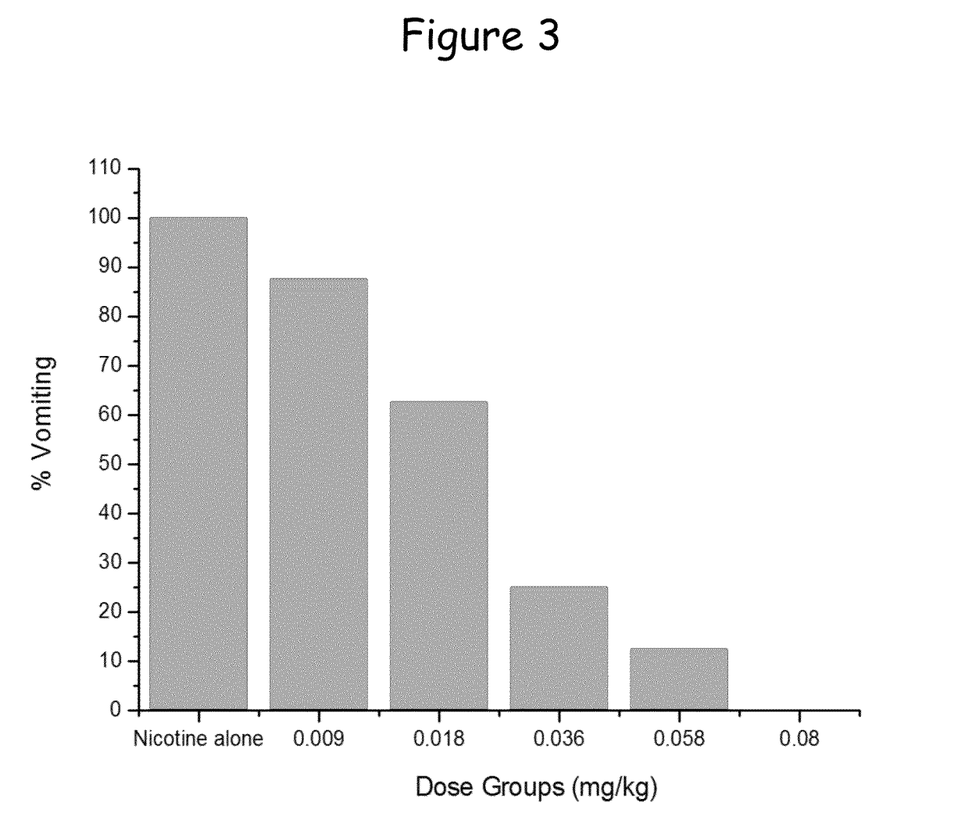
FIG. 3 is a bar graph showing the amount of protection from vomiting provided by 8-OH-DPAT compositions at varying dosages in female shrews in a model of emesis induced by nicotine tartarate.

The results of the foregoing tests are shown in FIG. 3. As can be seen in that figure, all of the animals not treated with the test compound, i.e. treated only with nicotine tartarate, experienced emesis, while the treated animals experienced reduced or no emesis in a dose-dependent manner. Animals treated with 0.08 mg/kg of the test compound experienced no emesis.

Figure 4:
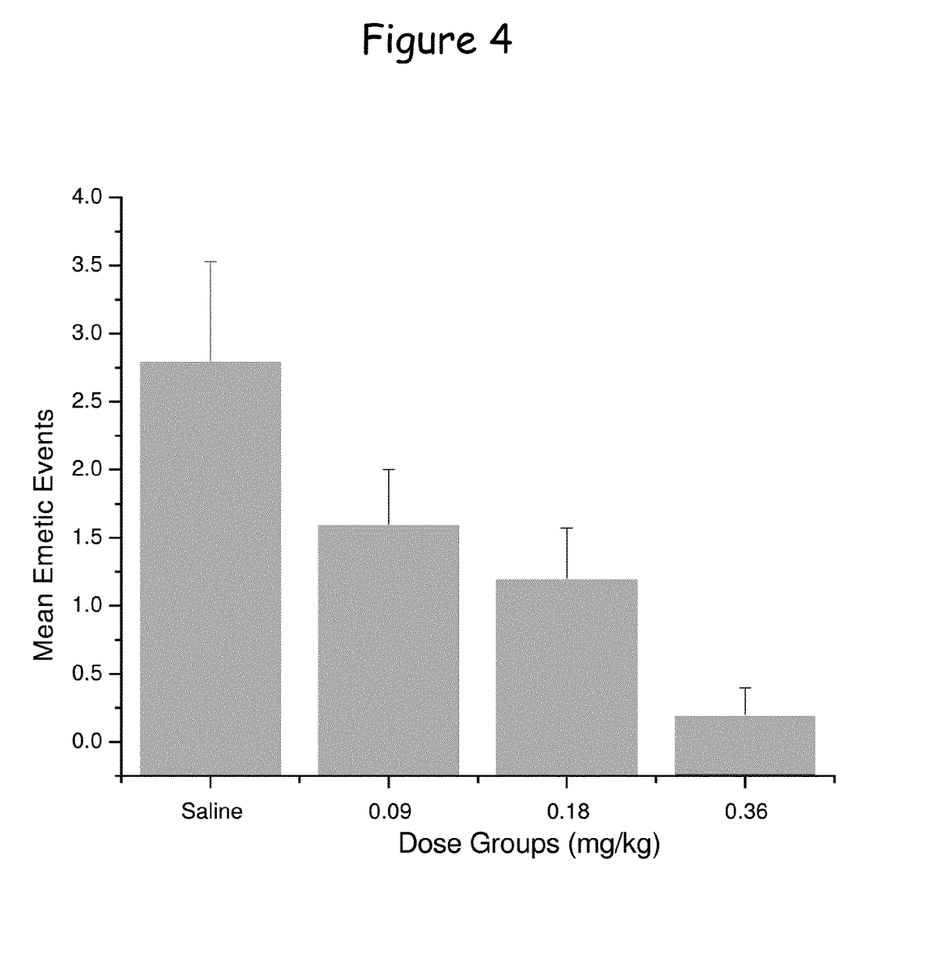
FIG. 4 is a bar graph showing the amount of protection from vomiting provided by 8-OH-DPAT compositions at varying dosages in female shrews in a model of emesis induced by cisplatin.

A group of shrews were also tested for emesis in response to the administration of 20 mg/kg of cisplatin intraperitoneally using the protocol described above, except that the test compound was administered 30 minutes after cisplatin administration. The results are shown in FIG. 4, which shows a reduction in emesis in the treated animals in a dose-dependent manner, with animals receiving at least 0.036 mg/kg of the test compound exhibiting a statistically significant reduction in symptoms of emesis.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. A method for screening candidate compounds, comprising the steps of:
    contacting one or more candidate compounds with a 5-$HT_{1a}$ receptor and determining the binding affinity and compound efficacy of the candidate compounds with respect to binding of the 5-$HT_{1a}$ receptor;
    contacting one or more candidate compounds with a 5-$HT_{1d}$ receptor and determining the binding affinity and compound efficacy of the candidate compounds with respect to binding of the 5-$HT_{1d}$ receptor;
    contacting one or more candidate compounds with a 5-$HT_7$ receptor and determining the binding affinity and compound efficacy of the candidate compounds for the 5-$HT_7$ receptor;
    selecting a candidate compound, wherein the selected candidate compound is an agonist of at least one of the 5-$HT_{1a}$ receptor and the 5-$HT_{1d}$ receptor, wherein the selected candidate compound is an antagonist of the 5-$HT_7$ receptor, and wherein the candidate compound has an EC50 value for the 5-$HT_7$ receptor of greater than 10 µM; and
    treating a subject for emesis by administering the selected candidate compound to the subject.

2. The method of claim 1, wherein the selected candidate compound has no binding affinity for the 5-$HT_7$ receptor.

3. The method of claim 1, wherein the selected candidate compound is an antagonist of the 5-$HT_7$ receptor.

4. The method of claim 1, wherein the selected candidate compound is an agonist of the 5-$HT_{1a}$ receptor.

5. The method of claim 1, wherein the selected candidate compound is an agonist of the 5-$HT_{1d}$ receptor.

6. The method of claim 1, further comprising the step of producing the selected compound.

7. The method of claim 1, wherein the 5-$HT_{1a}$ receptor is an endogenous 5-$HT_{1a}$ receptor.

8. The method of claim 1, wherein the 5-$HT_{1d}$ receptor is an endogenous 5-$HT_{1d}$ receptor.

9. The method of claim 1, wherein the candidate compound has an EC50 value for the 5-$HT_{1a}$ receptor of between 0.01 and 100 nanomolar in a predetermined assay.

10. The method of claim 1, wherein the candidate compound has an EC50 value for the 5-$HT_{1d}$ receptor of between 0.10 and 10,000 nanomolar in a predetermined assay.

11. The method of claim 1, wherein the candidate compound has a Ki of between 0.01 and 100 nanomolar for the 5-$HT_{1a}$ receptor.

12. The method of claim 11, wherein the candidate compound has a Ki of between 0.2 and 1.0 nanomolar for the 5-$HT_{1a}$ receptor.

13. The method of claim 1, wherein the candidate compound has a Ki of between 0.01 and 10,000 nanomolar for the 5-$HT_{1d}$ receptor.

14. The method of claim 13, wherein the candidate compound has a Ki of between 1.0 and 100 nanomolar for the 5-$HT_{1d}$ receptor.

15. The method of claim 1, wherein the candidate compound has anti-emetic activity.

* * * * *